(12) United States Patent
Minagawa et al.

(10) Patent No.: US 7,112,446 B2
(45) Date of Patent: Sep. 26, 2006

(54) METHOD FOR ANALYZING PROTEIN OR PEPTIDE

(75) Inventors: Hirotaka Minagawa, Tokyo (JP); Ichiro Ishida, Tokyo (JP); Akira Tsugita, Tokyo (JP); Takuji Nabetani, Tokyo (JP)

(73) Assignees: Tokyo Rikakikai Co., Ltd., Tokyo (JP); NEC Corporation, Tokyo (JP)

( * ) Notice: Subject to any disclaimer, the term of this patent is extended or adjusted under 35 U.S.C. 154(b) by 602 days.

(21) Appl. No.: 10/097,010

(22) Filed: Mar. 14, 2002

(65) Prior Publication Data

US 2004/0014229 A1 Jan. 22, 2004

(30) Foreign Application Priority Data

Mar. 14, 2001 (JP) ............................. 2001-072042

(51) Int. Cl.
*G01N 33/00* (2006.01)
(52) U.S. Cl. ....................................................... 436/86
(58) Field of Classification Search ................... 436/86
See application file for complete search history.

(56) References Cited

U.S. PATENT DOCUMENTS 5,521,097 A * 5/1996 Uchida et al. ................ 436/86
5,578,452 A * 11/1996 Shi et al. .................... 435/7.21
5,962,642 A * 10/1999 Tsugita et al. ............... 530/345
6,818,454 B1 * 11/2004 Goshe et al. ................ 436/173

OTHER PUBLICATIONS

"Experimental Medicine", Proteome Analytical Methods (published by Yodosha 2000), Chapter 2-II-4b and Chapter 2-IV, pp. 85-91 and 111-122.

A. Tsugita et al., "Application of chemical selective cleavage methods to analyze post-translational modification in proteins", *Proteomics 2001*, vol. 1, pp. 1082-1091.

* cited by examiner

*Primary Examiner*—Monique T. Cole
(74) *Attorney, Agent, or Firm*—Sughrue Mion, PLLC (57) ABSTRACT

In a method for efficiently analyzing a posttranslational modification of a protein using no enzyme, a protein or peptide to be analyzed is reacted with an acid (a thioester or hydrazine) under certain conditions. This makes it possible to detect variously modified states of a protein or peptide, whereby the identification of each specific modifying group and the position of each modified amino acid can be efficiently analyzed using a chemical method and a mass spectrometric apparatus.

9 Claims, 6 Drawing Sheets

METHOD FOR ANALYZING PROTEIN OR PEPTIDE

BACKGROUND OF THE INVENTION

1. Field of the Invention

The present invention relates to a method for analyzing a protein or peptide and, more particularly, to a method for structural analysis of a posttranslational modified state of a protein or peptide by the use of no enzyme.

2. Description of the Related Art

Many proteins are variously modified after their translation. Of the modifications, phosphorylation is a principal posttranslational modification among the modifications which change physiological activities and enzymatic activities of various proteins and direct intracellular signal transmission or intracellular metabolic activity.

As the methods for detecting the phosphorylation of a protein, a method of using a radioisotope or a method of using an antibody and the like have been known (e.g., Proteome Variation Analysis by Isotope Labeling, pp. 111–122, by Oda, Detection of Phosphorylated Proteins, pp. 85–91, by Yanagida and Takahashi, Additional vol. of Experimental Medicine, Proteome Analytical Methods, 2000, Yodosha).

However, the method of using a radioisotope is defective since tyrosine phosphorylation cannot be discriminated from serine phosphorylation or threonine phosphorylation and also special facilities and an exclusive apparatus are necessary.

Moreover, the method of using an antibody has a defect that phosphorylated amounts between different proteins in a sample cannot be simply compared because, even when the same phosphorylated amino acid-recognizing antibody is used, bonding specificity of the antibody varies depending on the kind of protein containing a phosphorylated amino acid, and thus an enzyme immunoassay is required for determining the phosphorylation, which invites an increase in number of steps.

There has been no method which determines not only phosphorylation but also variously modified state of a protein or peptide such as sulfation or glycosylation at high accuracy and efficiency.

SUMMARY OF THE INVENTION

A technical objective of the present invention is to provide a method for analyzing a protein or peptide using no enzyme or no special apparatus, particularly a novel analyzing method capable of structural analysis of a posttranslational modified state thereof.

The present invention provides a technology including a process wherein an acid is reacted with a protein or peptide to be analyzed, a technology wherein the acid is pentafluoropropionic acid or heptafluorobutyric acid, a technology wherein the acid contains dithiothreitol (DTT) or mercaptoethanol, a technology wherein the reaction temperature ranges from 30° C. to 90° C., a technology wherein the reaction time ranges from 6 hours to 16 hours, a technology wherein the reaction is carried out in a liquid phase or a gas phase, a technology wherein the above acid is replaced by S-ethyl trifluorothioacetate ($CF_3COSC_2H_5$), and a technology wherein the above acid is replaced by hydrous hydrazine ($NH_2NH_2 \cdot nH_2O$: n is an integer).

Namely, according to the invention, the following methods are afforded:

A method for analyzing a protein or peptide using a reaction process between the protein or peptide and an acid, wherein the above protein or peptide is reacted with at least one of the acids represented by the chemical formula; $C_mF_{2m+1}COOH$ (wherein m is a positive integer) or a derivative thereof or an aqueous solution thereof;

The method for analyzing a protein or peptide according to the above method, wherein the above acid or aqueous solution thereof is pentafluoropropionic acid ($C_2F_5COOH$) or heptafluorobutyric acid ($C_3F_7COOH$), or a pentafluoropropionic acid ($C_2F_5COOH$) aqueous solution or a heptafluorobutyric acid ($C_3F_7COOH$) aqueous solution;

The method for analyzing a protein or peptide according the above methods, wherein the above acid contains dithiothreitol (DTT) or β-mercaptoethanol;

The method for analyzing a protein or peptide according to any one of the above methods, wherein the concentration of the above acid aqueous solution ranges from 0.2% to 5%;

The method for analyzing a protein or peptide according to any one of the above methods, wherein the reaction temperature ranges from 30° C. to 90° C.;

The method for analyzing a protein or peptide according to any one of the above methods, wherein the reaction time ranges from 4 hours to 24 hours;

The method for analyzing a protein or peptide according to any one of the above methods, wherein the reaction is a liquid phase reaction or a gas phase reaction;

The method for analyzing a protein or peptide according to any one of the above methods, wherein S-ethyl trifluorothioacetate ($CF_3COSC_2H_5$) is used as a derivative of the above acid except liquid phase reaction; and The method for analyzing a protein or peptide according to any one of the above methods, wherein, as the above acid aqueous solution, hydrous hydrazine ($NH_2NH_2 \cdot nH_2O$: n is an integer) is used instead of the above $C_mF_{2m+1}COOH$.

Thus, according to the methods of the invention, variously modified state of a protein or peptide, such as phosphorylation, sulfation, or glycosylation, can be detected. A modified protein or peptide can be efficiently analyzed by eliminating a modifying group from a peptide fragment containing a specific modified amino acid by a chemical treatment, followed by analysis on a mass spectrometric apparatus or the like.

DESCRIPTION OF PREFERRED EMBODIMENTS

The following will explain the embodiments of the present invention with reference to the drawings.

Figure 1:
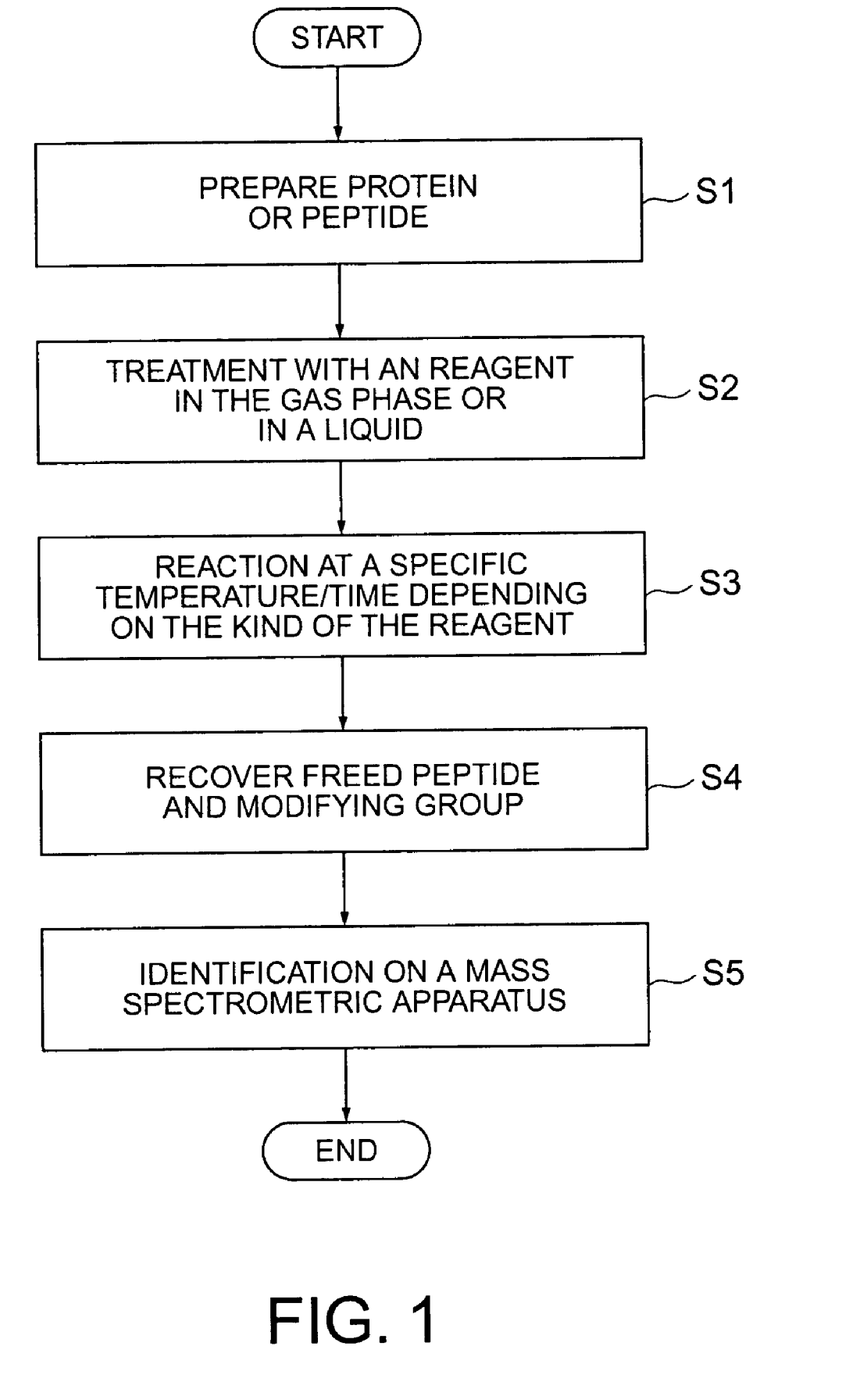
FIG. 1 is a flow chart illustrating a series of processes showing the basic concept of the invention, which specifies the modified group and modified site of a protein or peptide.

FIG. 1 is a conceptual flow chart illustrating a series of processes of the technologies common to each embodiment of the invention.

As shown in FIG. 1, the invention comprises steps of preparing a protein or peptide (Step S1), next, treating it with a reagent in a gas phase or in a liquid (Step S2), next, reacting it at a specific temperature and for a specific period of time depending on the kind of the reagent (Step S3), further recovering a freed peptide and a modifying group (Step S4), and identifying them on a mass spectrometric apparatus (Step S5).

Next, the embodiments of the invention will be explained in further detail.

First Embodiment

A peptide of a heat shock protein was used as a model substance to be tested for evidencing the effect of the invention. This peptide was phosphorylated and was known to have an amino acid sequential structure of the sequence: CLNRQLS($PO_3H_2$)SGVSEIR (hereinafter, referred to as Sequence 1), which was represented in accordance with one letter-abbreviation form. Namely, it is composed of 14 amino acid residues and has three serine residues (S: Ser) in the sequence, only the Ser at the seventh position from the N-terminus being phosphorylated. In the present embodiment, the peptide was used as a sample substance to be tested, and the information on the phosphorylation was pursued.

As a reaction vessel, a glass tube vessel (13×100 mm) was used. First, 300 pmol of the peptide dried under reduced pressure was placed into the vessel. For the vessel used by the present inventors, an amount of about 5 to 500 pmol is appropriate. Then, to the same vessel was added a 0.2% aqueous solution of pentafluoropropionic acid ($C_2F_5COOH$) manufactured by Sigma Chemical Co. containing 100 µl of 5% dithiothreitol (DTT) manufactured by Nacalai Tesque. Thereafter, the whole glass tube was depressurized and charged with argon gas (Ar), followed by sealing. The glass tube was maintained at 90° C. for 8 hours to react the sample with the pentafluoropropionic acid containing dithiothreitol (DTT) in a liquid phase.

Figure 2:
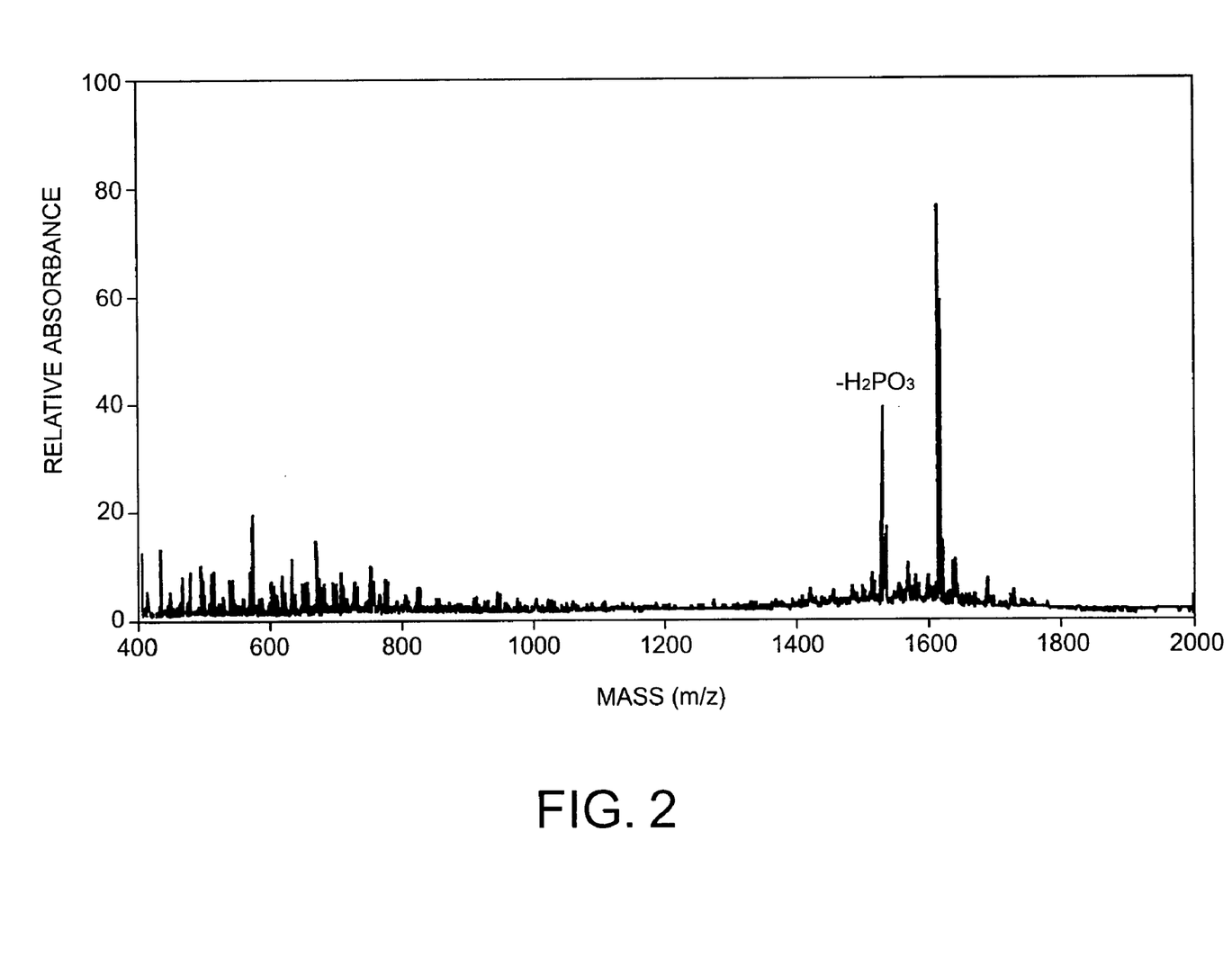
FIG. 2 is a chart for explaining first embodiment, showing a result of elimination of 30% of phosphoryl group ($H_2PO_3$).

Then, the sample was dried under vacuum and dissolved in 2 µl of 67% acetic acid. A 1 µl portion thereof was mixed with 1 µl of m-nitrobenzyl alcohol ($O_2NC_6H_4CH_2OH$), and the mixture was analyzed on a fast atom bombardment mass spectrometer (HX-110MS: manufactured by JEOL). Accelerating voltage was 10 kV and xenon gas was used as an ionizing gas. As a result, elimination of 30% of the phosphoryl group was observed as shown in FIG. 2.

Namely, according to the invention, it was confirmed that the presence of phosphorylation of a protein or peptide could be verified using no enzyme.

By subjecting the present protein to the treatment described in the present embodiment, the protein is divided into several specific peptides beforehand and, on each of the peptides, elimination of phosphoryl group also occurs at the same time, whereby it is understood that the specific peptide from which phosphoryl group is eliminated have been originally phosphorylated.

Thus, according to the invention, a phosphorylated site of a protein or peptide can be conveniently specified using no enzyme.

Second Embodiment

A peptide of tyrosine phosphatase was used as a second embodiment. This peptide was phosphorylated and was known to have an amino acid sequential structure of the sequence: Y($PO_3H_2$)PVML (hereinafter, referred to as Sequence 2), which was represented in accordance with one letter-abbreviation form.

Namely, this peptide composed of 5 amino acid residues was phosphorylated at the tyrosine reside present at the N-terminus. In the present embodiment, it was used as a sample substance to be tested, and the information on the phosphorylation was pursued.

As a reaction vessel, a vessel wherein large and small double glass tubes were nested was used. First, 300 pmol of the peptide was placed into the small glass tube (6×40 mm). Although the amount of the sample depends on a vessel, an amount of about 5 to 500 pmol is appropriate for the vessel used by the present inventors. To the same tube was added 100 µl of a 0.2% aqueous solution of pentafluoropropionic acid ($C_2F_5COOH$) manufactured by Sigma Chemical Co. containing 100 µl of 5% dithiothreitol (DTT) manufactured by Nacaki Tesque. Then, the whole glass tube was depressurized and charged with argon gas (Ar), followed by sealing. The glass tube was maintained at 90° C. for 8 hours to react the sample with the pentafluoropropionic acid containing dithiothreitol (DTT) in a gas phase.

The above reaction process may be carried out in a liquid phase as described in the first embodiment.

Figure 3:
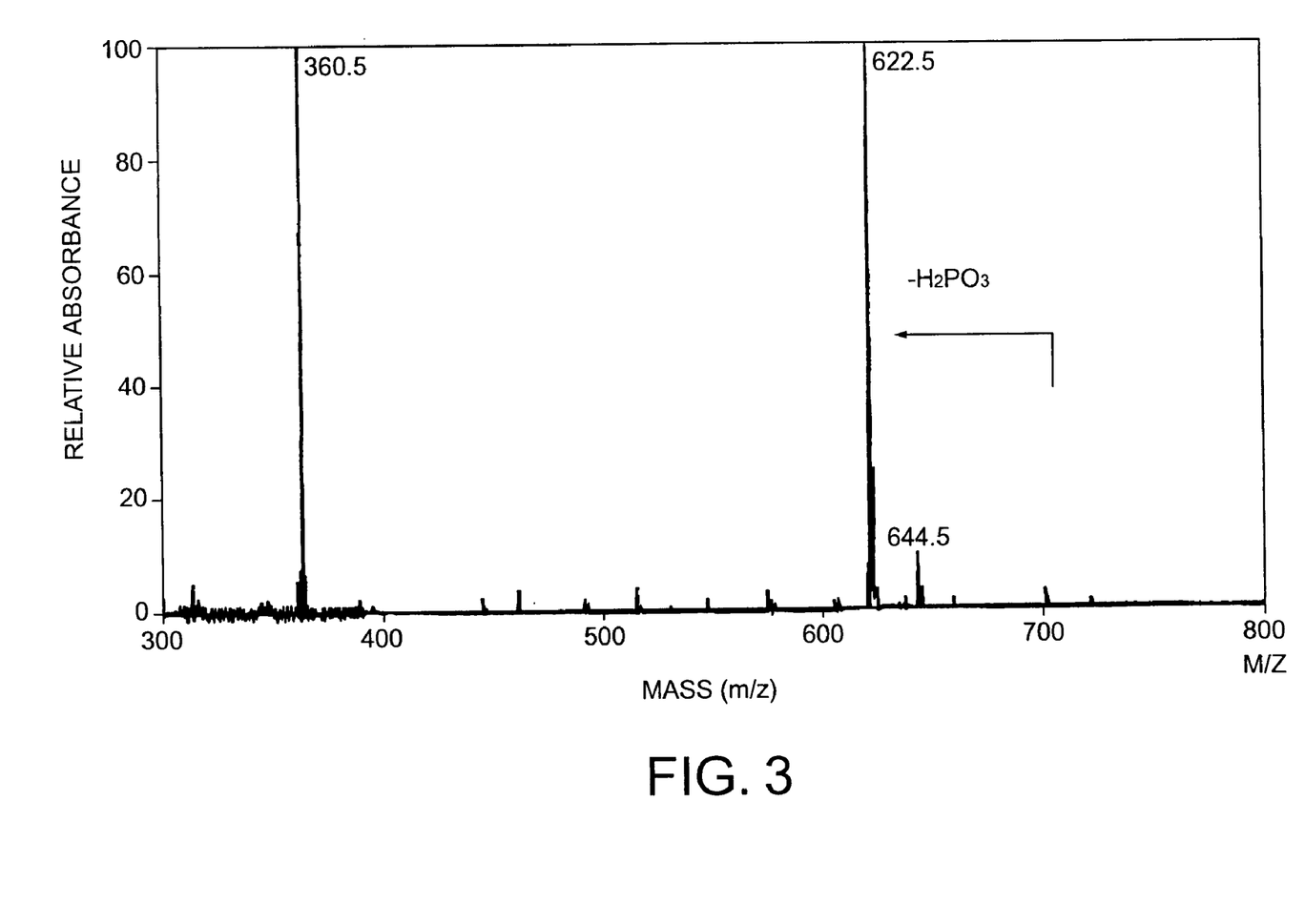
FIG. 3 is a chart for explaining second embodiment, showing a result of elimination of 100% of phosphoryl group ($H_2PO_3$).

Then, the sample was dried under vacuum and dissolved in 2 µl of 67% acetic acid. A 1 µl portion thereof was mixed with 1 µl of m-nitrobenzyl alcohol ($O_2NC_6H_4CH_2OH$), and the mixture was analyzed on a FAB mass spectrometer (HX-110MS: manufactured by JEOL). Accelerating voltage was 10 kV and xenon gas was used as an ionizing gas. As a result, elimination of 90% of the phosphoryl group was observed as shown in FIG. 3.

Namely, according to the invention, it was confirmed that the presence of phosphorylation of a protein or peptide could be verified using no enzyme.

By subjecting the present protein to the treatment described in the present embodiment, the protein is divided into several peptides and, on each of the peptides, elimination of phosphoryl group occurs at the same time, whereby it is understood that the specific peptide from which phosphoryl group is eliminated have been originally phosphorylated.

Thus, according to the invention, a phosphorylated site of a protein or peptide can be conveniently specified using no enzyme.

Third Embodiment

A peptide composed of the amino acid sequence: DY-($SO_3H$)MGMDF—$NH_2$ (amino acids represented in accordance with one letter-abbreviation form) was used as third embodiment. In this peptide, a tyrosine residue was sulfated.

Into a small glass tube (6×40 mm) was placed 50 pmol of DY-($SO_3H$)MGMDF—$NH_2$ dried under reduced pressure. Into a large glass tube (13×100 mm) was added 100 µl of S-ethyl trifluorothioacetate ($CF_3COSC_2H_5$) manufactured by Sigma Chemical Co. and the above small glass tube was inserted thereinto. Then, the whole large glass tube was depressurized and charged with argon gas (Ar), followed by sealing. The glass tube was maintained at 50° C. for 24 hours to promote the reaction. Herein, the tube may be maintained at 30° C. for 24 hours.

Thereafter, the sample was analyzed on a Matrix assisted laser desorption/ionization (MALDI)-time of flight (TOF)-mass spectrometer (MS), nitrogen laser, a double microchannel plate detector (apparatus: Voyager delayed-extraction RP TOF-MS, PerSeptive Biosystems, MA, USA/VSL-337ND: Laser Science, MA, USA; 337 nm; 3 nsec pulse length/Galileo, MA, USA).

Accelerating voltage of ion source was 20 kV, examination mode was leaner and delayed extraction. The sample dried under vacuum was dissolved in 2 µl of 0.1% trifluoroacetic acid, and 1 µl of the solution was mixed with 1 µl of the following matrix solution. The matrix solution was a mixed solution of 1 mg of sinapinic acid obtained from PerSeptive BioSystems (or 1 mg of α-cyano-4-hydroxycinnamic acid) and 100 µl of 0.1% trifluoroacetic acid, acetonitrile mixed solution (volume ratio 1:1). To the sample plate of the apparatus was inserted 1 µl of the solution, and the solvent was removed in the air at room temperature.

Figure 4:
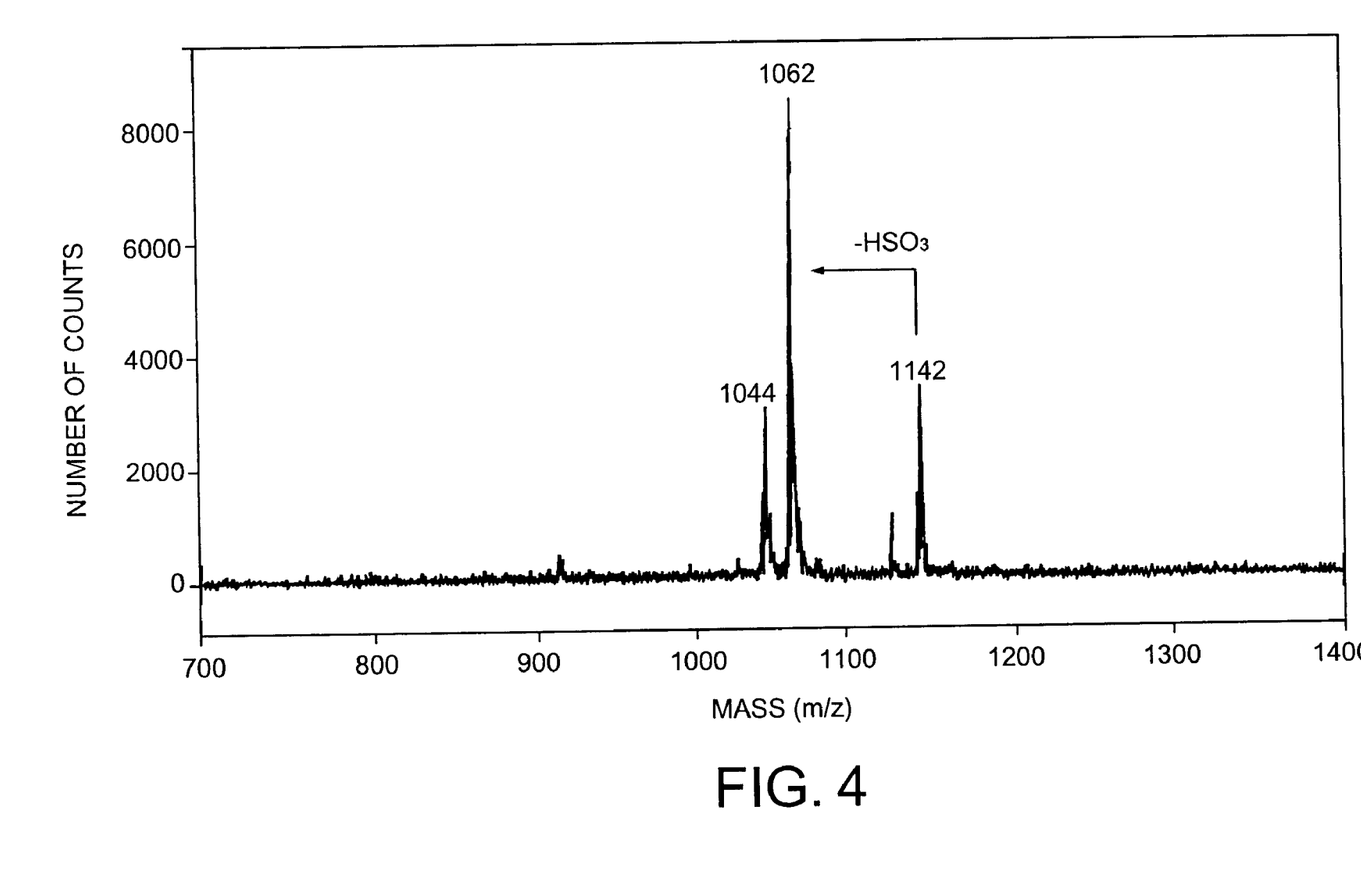
FIG. 4 is a chart for explaining third embodiment, showing a result of elimination of 75% of sulfate group ($HSO_3$).
Figure 5:
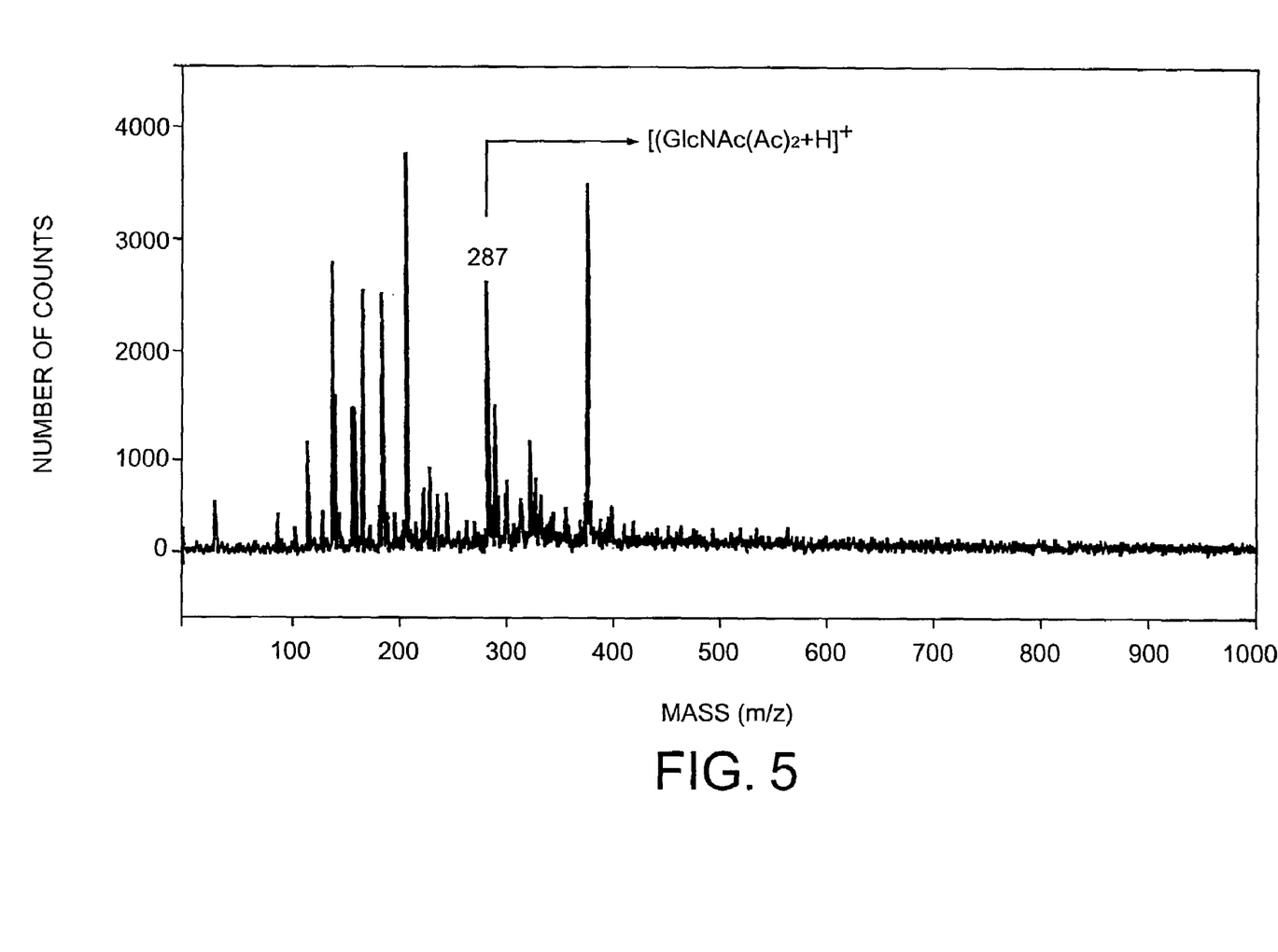
FIG. 5 is a chart for explaining fourth embodiment, showing a result of elimination of 100% of glycosylated group [(GlcNAc(Ac)$_2$)+H]$^+$.

The result of the mass spectrometry is shown in FIG. 4. From FIG. 4, it can be confirmed that 75% of the sulfate part ($HSO_3$) is eliminated from the sulfated tyrosine part ($HSO_3$-Tyr). Thus, according to the technology of the invention, a sulfated site of a protein or peptide can be conveniently specified using no enzyme.

Fourth Embodiment

As fourth embodiment, the following reaction was carried out using Fmoc-Asn(GlcNAc(Ac)$_3$) as a model peptide of a glycosylated asparagine (Asn N-glycosylation).

Into a small glass tube (6×40 mm) was placed 50 pmol of Fmoc-Asn(GlcNAc(Ac)$_3$) dried under reduced pressure. Into a large glass tube (13×100 mm) was added 100 µl of hydrous hydrazine ($NH_2NH_2.H_2O$ or $NH_2NH_2.4H_2O$), and the above small glass tube was inserted thereinto. Then, the whole large glass tube was depressurized and charged with argon gas (Ar), followed by sealing. The glass tube was maintained at 30° C. for 4 hours (or 16 hours) to promote a gas phase reaction. This reaction can be also carried out in a liquid phase. After the reaction, the sample was dried under vacuum and subjected to the same mass spectrometry as in the third embodiment, whereby elimination of 100% of glycosyl group was observed.

Fifth Embodiment

The three reactions were tested for Asn N-glycosylation and Ser/Thr O-glycosylation using Fmoc-Asn(GlcNAn(Ac)$_3$) ($M_r$683.3) and Fmoc-Ser(GalNAc(Ac)$_3$) ($M_r$656.2) as the respective model compounds. Both O-glycoside and N-glycoside bonds were observed unchanged by both Ser-N and Asp-C reactions, but almost completely deglycosylated by the Asn-C reaction, ($NH_2NH_2.H_2O$, 30° C., 4 h). The products were GlcNAc (AC)$_2$)+H(287 m/z) and GalNAc(Ac)$_2$)+H(287 m/z) respectively, losing each one acetyl group and amino acid [11]. The data are shown in FIGS. 6A through 6D.

Figures 6A, 6B:
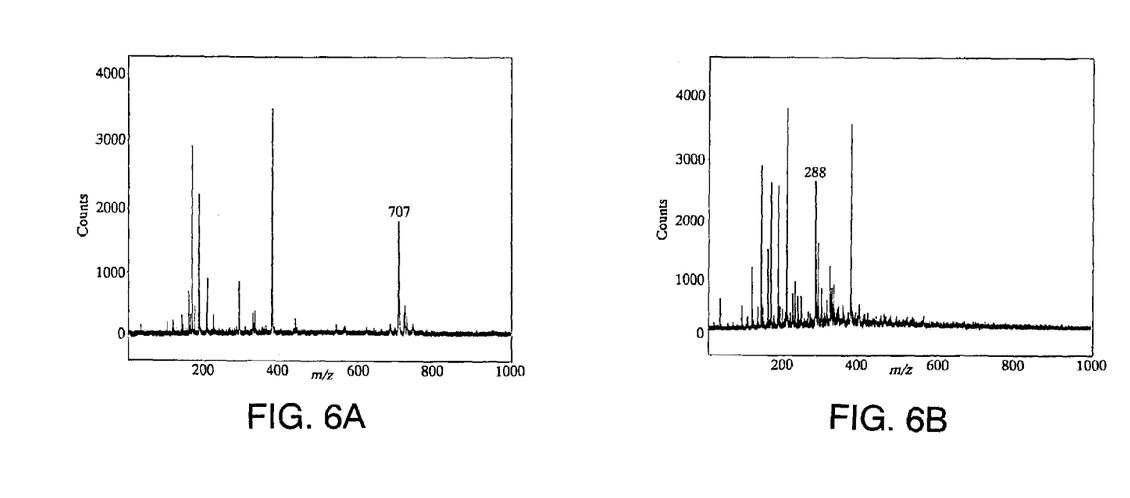
FIGS. 6A through 6D are charts for explaining fifth embodiment, showing MALDI-TOF-MS profiles of the reaction product of a $NH_2NH_2 \cdot H_2O$ vapor at 30° C. for 4 h.
Figure 6C:
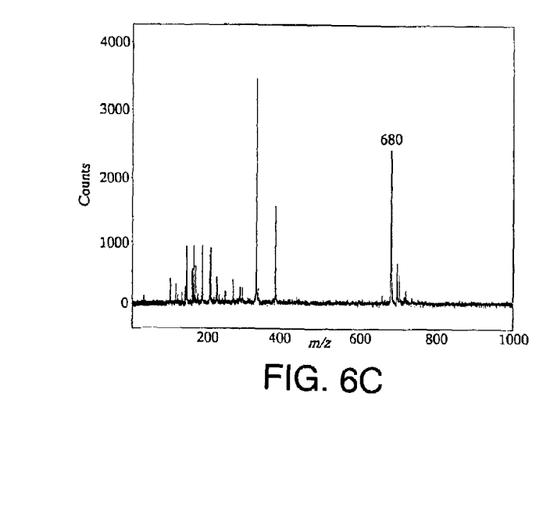
Figure 6D:
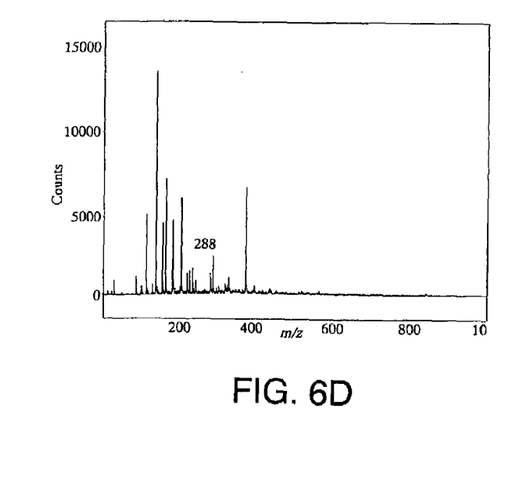

FIG. 6A represents untreated sample ($M_r$683.3); 707 m/z, [F-moc-Asn-(GLcNAc(AC)$_3$)+Na]$^+$, FIG. 6B represents reaction product; 287 m/z, [(GLcNAc(AC)$_2$)+H]$^+$), FIG. 6C represents untreated sample (Mr 656.2); 680 m/z, [F-moc-Ser-(GaLNAc(AC)$_3$)+Na]$^+$, and FIG. 6D represents reaction product; 287 m/z, [GaLNAc(AC)$_2$)+H]$^+$.

Thus, according to the invention, a glycosylated site of a protein or peptide can be conveniently specified using no enzyme.

As explained in the above, the present invention provides a method for analyzing a protein or peptide capable of detecting variously modified state of a protein or peptide such as phosphorylation, sulfation or glycosylation.

Moreover, the invention provides a method for analyzing a protein or peptide capable of analyzing a modified protein or peptide at high accuracy and efficiency by eliminating a modifying group from a peptide fragment containing a specific modified amino acid by a chemical treatment followed by determination by means of a mass spectrometry or the like.

What is claimed is:

1. A method for analyzing post-translational modification of a protein or peptide, comprising the steps of
   (a) obtaining a reaction mixture by reacting a protein or peptide suspected of being post-translationally modified with at least one acid represented by the formula: $C_mF_{2m+1}COOH$, wherein m is a positive integer of from 1 to 3, or a derivative of said acid, or an aqueous solution thereof, to partially eliminate modifying groups, and
   (b) analyzing the resulting reaction mixture of step (a) by mass spectrometry to determine the identity of one or more modifying groups and one or more sites at which said protein or peptide was modified,
   wherein said acid or aqueous solution thereof is pentafluoropropionic acid ($C_2F_5COOH$), heptafluorobutyric acid ($C_3F_7COOH$), a pentafluoropropioric acid ($C_2F_5COOH$) aqueous solution, or a heptafluorobutyiric acid ($C_3F_7COOH$) aqueous solution, and
   wherein said reaction mixture contains dithiothreitol (DTT) or β-mercaptoethanol.

2. A method for analyzing post-translational modification of a protein or peptide, comprising the steps of
   (a) obtaining a reaction mixture by reacting a protein or peptide suspected of being post-translationally modified with at least one acid represented by the formula: $C_mF_{2m+1}COOH$, wherein m is a positive integer of from 1 to 3, or a derivative of said acid, or an aqueous solution thereof, to partially eliminate modifying groups, and
   (b) analyzing the resulting reaction mixture of step (a) by mass spectrometry to determine the identity of one or more modifying groups and one or more sites at which said protein or peptide was modified,
   wherein said derivative is S-ethyl trifluorothioacetate ($CF_3COSC_2H_5$).

3. A method for analyzing post-translational modification of a protein or peptide, comprising the steps of
   (a) obtaining a reaction mixture by reacting a protein or peptide suspected of being post-translationally modified with at least one acid represented by the formula: $NH_2NH_2.nH_2O$ wherein n 1 or 4, or a derivative of said acid, or an aqueous solution thereof, to partially eliminate modifying groups, and
   (b) analyzing the resulting reaction mixture of step (a) by mass spectrometry to determine the identity of one or more modifying groups and one or more sites at which said protein or peptide was modified,
   wherein said reacting is only in a gas phase.

4. The method for analyzing a protein or peptide according to claim 3, wherein said reaction mixture contains dithiothreitol (DTT) or β-mercaptoethanol.

5. A method for analyzing post-translational modification of a protein or peptide, comprising the steps of
(a) obtaining a reaction mixture by reacting a protein or peptide suspected of being post-translationally modified with at least one acid represented by the formula: $C_mF_{2m+1}COOH$, wherein m is a positive integer of from 1 to 3, or a derivative of said acid, or an aqueous solution thereof, to partially eliminate modifying groups, and
(b) analyzing the resulting reaction mixture of step (a) by mass spectrometry to determine the identity of one or more modifying groups and one or more sites at which said protein or peptide was modified,
wherein said acid or aqueous solution thereof is pentafluoropropionic acid ($C_2F_5COOH$), heptafluorobutyric acid ($C_3F_7COOH$), a pentafluoropropioric acid ($C_2F_5COOH$) aqueous solution, or a heptafluorobutyiric acid ($C_3F_7COOH$) aqueous solution, and wherein said acid is present in said acid aqueous solution in the amount of from 0.1% to 5%.

6. The method for analyzing a protein or peptide according to claim 5, wherein said reacting is carried out at from 30° C. to 90° C.

7. The method for analyzing a protein or peptide according to claim 5, wherein said reacting is a liquid phase reaction or a gas phase reaction.

8. The method for analyzing a protein or peptide according to claim 5, wherein said post-translational modification is phosphosylation, sulfation, and/or glycosylation.

9. The method for analyzing a protein or peptide according to claim 8, wherein said glycosylation is Asn N-glycosylation and/or Ser O-glycosylation.

* * * * *